United States Patent [19]
Lemaire

[11] Patent Number: 5,858,791
[45] Date of Patent: Jan. 12, 1999

[54] METHOD AND DEVICE FOR THE CONTINUOUS MEASUREMENT OF VARIATIONS IN THE OVERALL SATURATION OF A SAMPLE WITH INCOMPRESSIBLE IMMISCIBLE FLUIDS

[75] Inventor: Christian Lemaire, Nanterre, France

[73] Assignee: Institute Francais du Petrole, Rueil-Malmaison, France

[21] Appl. No.: 931,944

[22] Filed: Sep. 17, 1997

Related U.S. Application Data

[63] Continuation of Ser. No. 574,545, Dec. 19, 1995, abandoned.

[30] Foreign Application Priority Data

Dec. 19, 1994 [FR] France .................................. 94 15375

[51] Int. Cl.⁶ .................................................. G01N 33/24
[52] U.S. Cl. ................................ 436/25; 73/38; 73/433; 73/434; 422/69; 436/31; 436/908
[58] Field of Search .............................. 436/25, 31, 908; 73/38, 433, 434; 422/69

[56] References Cited

U.S. PATENT DOCUMENTS

| | | |
|---|---|---|
| 2,687,037 | 8/1954 | Saxe . |
| 4,487,056 | 12/1984 | Wiley . |
| 4,543,821 | 10/1985 | Davis, Jr. . |
| 4,672,840 | 6/1987 | Cullick . |
| 4,679,421 | 7/1987 | Burree ........................................ 73/38 |
| 4,773,254 | 9/1988 | Shen .......................................... 73/38 |
| 5,086,643 | 2/1992 | Marek . |
| 5,209,104 | 5/1993 | Collins et al. . |
| 5,299,453 | 4/1994 | Sprunt et al. . |
| 5,425,265 | 6/1995 | Jaisinghani ................................ 73/38 |

OTHER PUBLICATIONS

Revue deL'Institut Francais Du Petrole, vol. 45, No. 4, Jul. 1990, Paris, FR. pp. 489–506.

*Primary Examiner*—Jan Ludlow
*Attorney, Agent, or Firm*—Antonelli, Terry, Stout & Kraus, LLP

[57] ABSTRACT

Saturation variations are obtained by displacing a first fluid (for example water) that initially saturates a sample (1) coated with resin (2) by injecting therein, through a first end plate or cap (3) and by means of a pump (7), a second fluid (for example oil). The mixture flowing out through an opposite end plate (4) is collected in an initially filled two-phase separator (9) placed on an electronic balance (10). The first excess fluid flows towards a vessel (13), and the progressive accumulation of the second fluid in separator (9) leads to a variation in the total weight. A programmed processor (14) computes permanently the saturation values of the sample with respect to the first and to the second fluid, from the measured weight variations of separator (9). The method and device can be used for laboratory measurements of rock samples for example.

14 Claims, 1 Drawing Sheet

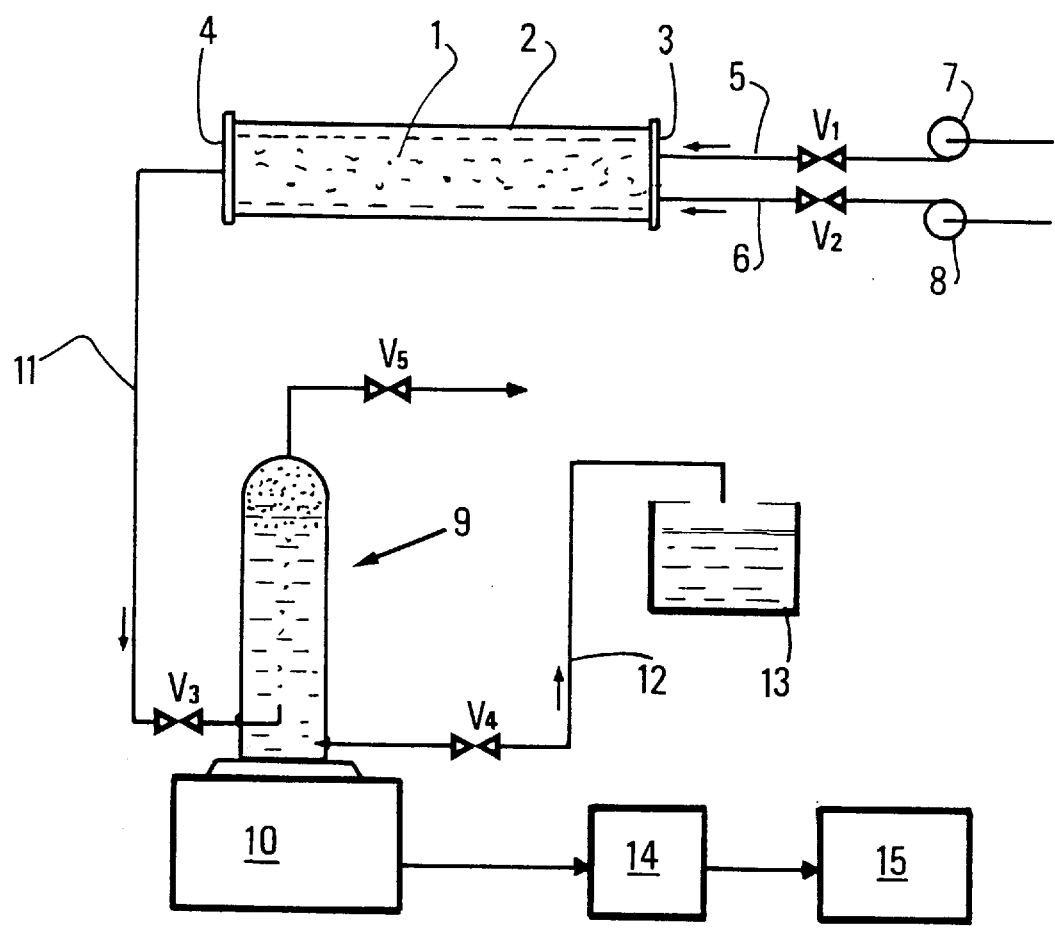

METHOD AND DEVICE FOR THE CONTINUOUS MEASUREMENT OF VARIATIONS IN THE OVERALL SATURATION OF A SAMPLE WITH INCOMPRESSIBLE IMMISCIBLE FLUIDS

This application is a Continuation application of application Ser. No. 08/574,545, filed Dec. 19, 1995 now abandoned.

BACKGROUND OF THE INVENTION

1. Field of the Invention

The present invention relates to a method of the continuous measurement of variations in the overall fluid saturation of a porous material sample subjected to drainage or to an imbibition phase, according to the principle of a continuous constant-volume weighing, and to a device for the implementation thereof.

The method according to the invention is notably suited for the study of geologic samples taken in formations containing or likely to contain petroleum effluents.

2. Description of the Prior Art

The knowledge that can be acquired concerning various petrophysical parameters of rocks during drainage or imbibition phases can be used for example for selecting the most appropriate fluid for displacing the petroleum effluents they contain and for improving thereby the efficiency of effluent enhanced recovery processes in a reservoir.

It is known to determine for example the saturation and the wettability of rocks with respect to fluids such as water (in the form of brine) and oil that can be contained therein. To that effect, rock drainage phases are carried out, i.e. a displacement of the fluids intended to decrease the water saturation, followed by imbibition phases which, on the contrary, are intended to increase its water saturation (Sw). The capillary pressure at a point of a porous sample in the presence of water and of oil in the continuous phase is defined, as it is well-known, as the difference Pc at equilibrium between the pressure P(oil) and the pressure P(water). Devices allowing petrophysical parameters of rocks to be measured are for example described in patent applications FR-2,603,040, EN-93/09,481 or EN-94/10,783 filed by the assignee or in U.S. Pat. Nos. 4,868,751 and 5,069,065.

SUMMARY OF THE INVENTION

The method according to the invention allows the determination automatically of the overall saturation variations of a sample exhibiting a certain porosity and that has initially been saturated with a first fluid, when a second fluid is injected therethrough.

The invention is characterized in that the fluids displaced out of the sample are collected in a two-phase separator initially filled with the first fluid, the weight variations of the separator due to the accumulation therein of the second fluid are measured continuously, and the variations with time in the overall saturation of the sample are calculated from these weight variations, knowing the values of the respective specific weights of the two fluids.

According to an implementation mode, the sample is initially saturated with water and this water is displaced out of the sample by injecting oil. Conversely, according to another implementation mode, the sample can be initially saturated with oil and this oil can be displaced out of the sample by injecting water.

The device for implementing the method comprises a two-phase separator initially filled with the first fluid, means for weighing the separator, producing signals indicative of the separator weight variations due to the accumulation therein of the second fluid, means for injecting the second fluid into the sample, means for collecting the fluids coming out of the sample and means for processing the signals produced by the weighing means in order to determine the saturation variations with time of the sample.

The separator comprises for example a cell provided with an inlet for a line intended to collect the fluids discharged from the sample, and with an outlet for the connection of a line allowing the first excess fluid to be discharged.

The signal processing means include for example a processor programmed to determine the saturation variations from the weight variations of the separator and from the respective specific weights of the first and of the second fluid.

The method and the device according to the invention thus allow the determination automatically as a function of time and over long periods a whole process of progressive saturation of a sample in contact with two different fluids.

BRIEF DESCRIPTION OF THE DRAWING

The method for measuring the variations in the overall saturation of a sample according to the invention can be implemented for example with the device schematized in FIG. 1, which will be described hereafter by way of a non limitative example.

DESCRIPTION OF THE PREFERRED EMBODIMENTS

The sample bar 1 to be tested is tightly coated for example with a resin sheath 2 providing a lateral seal. Two end plates or caps 3, 4 rest directly on the end walls of the bar at both ends of the sheath. The first end plate 3 is provided with bores for the connection with pipes 5 and 6 communicating, by means of valves V1, V2, with a water injection pump 7 and/or an oil injection pump 8.

Selective pressure taps provided with semipermeable membranes PP such as those described for example in the assignee's patent application EN-94/15376 can also be inserted through the sheath in various places along the sample, so as to measure selectively the pressures of the different phases in the sample and to allow for example capillary pressures to be calculated.

The device further comprises a phase separator 9 consisting of an elongated vessel or cell made of glass for example, that is placed on a balance 10. Cell 9 communicates with the opposite end plate 4 by means of a line 11 provided with a control valve V3, that opens to the base thereof. Another line 12 provided with a control valve V4 communicates the lower part of separator 9 with a collecting vessel 13. An upper port controlled by another valve V5 allows a possible gas phase to escape from separator 9. Balance 10 is of the electronic type. The measuring signals relative to the weight of separator 9 and delivered by balance 10 are applied to an acquisition inlet of processor 14 programmed to perform the follow-up of tests as described hereafter, this processor being connected to a control console 15.

A dry porous sample is used for example, that is first saturated under vacuum with brine. An irreducible water saturation is then achieved, this operation consisting for example in injecting oil with a constant flow rate into the saturated sample by means of pump 8, until a minimum irreducible water saturation level is reached. Separator 9 and line 11 are totally filled with brine, and balance 10 is initialized at zero.

Valve V1 is closed and, valves V1, V3 and V4 being open, water is injected through plate 3 into test bar 1 by means of pump 7. A mixture consisting of water and of oil displaced by the injection flows out through line 11 and enters separator 9. The oil accumulates in the upper part of cell 9 and the excess water escapes towards collecting vessel 13. The weight of separator 9 globally decreases and balance 10 records a negative weight variation with respect to the initial zero.

From the negative variations in the weight M(t) as a function of time (t) recorded by balance 10 and acquired by processor 14, the latter computes continuously the symmetrical variations in the oil volume Vo and the water volume Vw in cell 9 by means of the following relations:

$$Vo=-M(t)/(Ro-Rw); \text{ and}$$

$$Vw=M(t)/(Rw-Ro),$$

(Rw–Ro) representing the difference of the specific weights of the water and of the oil respectively. Processor 14 also determines the variations with time in the water and oil saturations of the sample with respect to the pore volumes of the bar.

A water displacement process in a rock sample by means of injected oil has been described by way of example. It is obvious that an oil displacement in a sample by means of injected water can also be tested under the same conditions, by changing of course the position of the ports communicating separator 9 with lines 11, 12 accordingly.

More generally, the method described is suited for any process where a first saturating fluid is displaced in a sample by injecting a second fluid, both fluids being immiscible and incompressible.

The layout described above allows the course of a two-phase saturation process to be followed automatically over long periods.

I claim:

1. A method of measuring variations of saturation of a porous sample in a device including a multiphase separator and a weighing device for weighing the multiphase separator, the method comprising:

initially filling completely the separator with a first fluid having a first known density;

saturating the sample with the first fluid;

injecting into the sample a second fluid having a second known density different from the first density, so as to displace the first fluid and form a mixed stream;

introducing the mixed stream into the separator while evacuating the first fluid from the separator so as to keep the separator full while retaining the second fluid in the separator;

measuring the weight of the separator while introducing the mixed stream; and determining the variations of the saturation of the sample from the measured weight and known densities.

2. A method as claimed in claim 1 wherein:

the weighing device continuously measures the weight of the separator while introducing the mixed stream; and the variations of the saturation of the sample are determined continuously from the measured weight and known densities.

3. A method as claimed in claim 1, wherein the first fluid initially saturating the sample is water and the second fluid injected in the sample is oil.

4. A method as claimed in claim 3 wherein:

the weighing device continuously measures the weight of the separator while introducing the mixed stream; and the variations of the saturation of the sample are determined continuously from the measured weight and known densities.

5. A method as claims in claim 1, wherein the first fluid initially saturating the sample is oil and the second fluid injected in the sample is water.

6. A method as claimed in claim 5 wherein:

the weighing device continuously measures the weight of the separator while introducing the mixed stream; and the variations of the saturation of the sample are determined continuously from the measured weight and known densities.

7. A device for measuring variations of saturation of a porous sample, the device comprising:

a multiphase separator initially filled completely with a first fluid having a first known density;

a first fluid handling system which saturates the sample with the first fluid;

an injector which injects a second fluid into the sample with the second fluid having a second known density different from the first density, so as to displace the first fluid and form a mixed stream;

a fluid transporting system which introduces the mixed stream into the separator while evacuating the first fluid from the separator so as to keep the separator full while retaining the second fluid in the separator;

a weighing device which measures the weight of the separator while introducing the mixed stream; and a processor which determines the variations of the saturation of the sample from the measured weight and known densities.

8. A device as claimed in claim 7 wherein:

the weighing device continuously measures the weight of the separator while introducing the mixed stream; and the processor continuously determines the variations of the saturation of the sample from the measured weight and known densities.

9. A device as claimed in claim 7, wherein:

the processor is programmed to determine the variations of saturation from variations in weight of the multiphase separator and from respective known densities of the first and of the second fluids.

10. A device as claimed in claim 9 wherein:

the weighing device continuously measures the weight of the separator while introducing the mixed stream; and the processor continuously determines the variations of the saturation of the sample from the measured weight and known densities.

11. A device as claimed in claim 7, wherein:

the multiphase separator comprises a cell provided with an inlet and an outlet; and the outlet is connected with an exhaust line for discharging an excess of the first fluid to be discharged.

12. A device as claimed in claim 11 wherein:

the weighing device continuously measures the weight of the separator while introducing the mixed stream; and the processor continuously determines the variations of the saturation of the sample from the measured weight and known densities.

13. A device as claimed in claim 11, wherein:

the processor is programmed to determine the variations of saturation from variations in weight of the separator and from respective known densities of the first and of the second fluids.

14. A device as claimed in claim 13 wherein:

the weighing device continuously measures the weight of the separator while introducing the mixed stream; and the processor continuously determines the variations of the saturation of the sample from the measured weight and known densities.

* * * * *